United States Patent
Vogel (10) Patent No.: US 9,757,013 B2
(45) Date of Patent: Sep. 12, 2017

(54) OPTICS TUBE FOR AN ENDOSCOPE, ROD LENS, COMBINATION OF AN OPTICS TUBE AND AT LEAST ONE ROD LENS, AND ENDOSCOPE

(71) Applicant: Karl Storz GmbH & Co. KG, Tuttlingen (DE)

(72) Inventor: Walter Vogel, Tuttlingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 521 days.

(21) Appl. No.: 14/282,391

(22) Filed: May 20, 2014

(65) Prior Publication Data

US 2014/0350344 A1    Nov. 27, 2014

(30) Foreign Application Priority Data

May 22, 2013    (DE) .......................... 10 2013 105 233

(51) Int. Cl.
| | | |
|---|---|---|
| *A61B 1/04* | (2006.01) |
| *A61B 1/00* | (2006.01) |
| *A61B 1/002* | (2006.01) |
| *G02B 23/24* | (2006.01) |

(52) U.S. Cl.
CPC .......... *A61B 1/00112* (2013.01); *A61B 1/002* (2013.01); *A61B 1/0011* (2013.01); *G02B 23/2407* (2013.01); *G02B 23/2476* (2013.01); *A61B 1/00096* (2013.01)

(58) Field of Classification Search
USPC .......................... 600/128–130, 138; 359/903
See application file for complete search history.

(56) References Cited

U.S. PATENT DOCUMENTS

| | | | | |
|---|---|---|---|---|
| 3,896,463 A * | 7/1975 | Laskey | .................. | G03B 17/12 |
| | | | | 359/903 |
| 4,047,802 A * | 9/1977 | Pieters | ..................... | B60Q 1/26 |
| | | | | 359/549 |
| 4,608,966 A * | 9/1986 | Storz | ...................... | A61B 1/002 |
| | | | | 359/654 |
| 5,423,761 A * | 6/1995 | Hein | ................... | A61B 1/00137 |
| | | | | 251/149.2 |
| 5,706,143 A * | 1/1998 | Hipp | .................. | G02B 23/2476 |
| | | | | 126/4 |
| 5,933,287 A | 8/1999 | Muller | | |
| 6,299,220 B1 * | 10/2001 | Dittrich | ............. | A61B 1/00128 |
| | | | | 285/317 |

(Continued)

FOREIGN PATENT DOCUMENTS

| | | |
|---|---|---|
| DE | 19732991 A1 | 2/1999 |
| DE | 102006041920 A1 | 3/2008 |

(Continued)

*Primary Examiner* — Matthew J Kasztejna
(74) *Attorney, Agent, or Firm* — Whitmyer IP Group LLC (57) ABSTRACT

An optics tube for an endoscope including a magnet arrangement which extends parallel to a longitudinal axis of the optics tube. A rod lens including a rod-shaped lens unit made of a rod-shaped lens element or a plurality of lens elements cemented to one another, wherein, on one side on the circumferential face thereof, the lens unit includes a magnet arrangement. The invention also relates to a combination of an optics tube and a rod lens, and to an endoscope.

16 Claims, 4 Drawing Sheets

(56) References Cited

U.S. PATENT DOCUMENTS

| | | | | |
|---|---|---|---|---|
| 6,398,723 B1* | 6/2002 | Kehr | ............ | G02B 7/001 |
| | | | | 359/385 |
| 6,641,531 B2* | 11/2003 | Kehr | ............ | A61B 1/00165 |
| | | | | 600/172 |
| 7,229,406 B2* | 6/2007 | Kehr | ............ | A61B 1/00183 |
| | | | | 600/172 |
| 8,033,987 B2* | 10/2011 | Lehmann | ............ | A61B 1/00126 |
| | | | | 359/827 |
| 2007/0219414 A1* | 9/2007 | Lei | ............ | G02B 23/2446 |
| | | | | 600/173 |
| 2008/0062540 A1 | 3/2008 | Scholer | | |
| 2008/0183042 A1* | 7/2008 | Lederer | ............ | G02B 23/2407 |
| | | | | 600/160 |
| 2011/0210689 A1* | 9/2011 | Vogel | ............ | A61B 1/00188 |
| | | | | 318/631 |
| 2014/0235947 A1* | 8/2014 | Dahmen | ............ | A61B 1/00096 |
| | | | | 600/129 |
| 2014/0340743 A1* | 11/2014 | Vogel | ............ | G02B 7/02 |
| | | | | 359/435 |

FOREIGN PATENT DOCUMENTS

| | | |
|---|---|---|
| DE | 102010000582 A1 | 9/2011 |
| EP | 1320319 B1 | 12/2003 |
| JP | 2012080944 A | 4/2012 |

\* cited by examiner

OPTICS TUBE FOR AN ENDOSCOPE, ROD LENS, COMBINATION OF AN OPTICS TUBE AND AT LEAST ONE ROD LENS, AND ENDOSCOPE

FIELD OF THE INVENTION

The present invention relates to an optics tube for an endoscope, a rod lens, a combination of an optics tube and at least one rod lens, and an endoscope.

BACKGROUND OF THE INVENTION

Endoscopes are used to view cavities in the human or animal body and also in technical objects. An endoscope typically comprises an elongate endoscope shank, which is suitable for insertion into the cavity to be viewed, and a head that can have attachments and control elements and also an eyepiece lens. Inside the endoscope shank and the head there is an optical system for transmitting an endoscopic image from the distal end of the endoscope, i.e. the end remote from the observer, to the proximal end, i.e. the end near the observer. For this purpose, the optical system comprises in particular a distally arranged objective for receiving the endoscopic image, an image carrier, and an eyepiece arranged at the proximal end of the endoscope, with an eyepiece lens for viewing the transmitted endoscopic image. The endoscope can be designed in particular as a rigid endoscope with a rigid endoscope shank and can have, as its image carrier, an arrangement of rod lenses accommodated in an optics tube arranged inside the endoscope. Moreover, the endoscope can have an illuminating device for illuminating the cavity to be viewed, and, if appropriate, it can have further devices, such as channels for endoscopic work instruments.

When assembling the optical components in the optics tube of a rigid endoscope, they are usually pushed into the optics tube from the proximal side in the sequence and arrangement predefined by the calculation of the optical system. In particular, the objective and one or more rod lenses, as well as, optionally one or more aperture stops and/or spacers are pushed in succession into the optics tube. For this purpose, the optical components have an external diameter that is slightly smaller than the internal diameter of the optics tube. With the aid of a system spring and a system closure guide, the entire optical system is pretensioned in the distal direction and thereby held against a distal closure piece of the optics tube, which can be provided in particular by a cover glass. What this achieves is that the optical elements, in particular the rod lenses, are assembled in a simple manner at the predetermined axial position thereof in the optics tube and can be removed again during a repair.

During use, endoscopes are exposed to significant mechanical loads, in particular accelerations or tremors and bending. Here, the optical elements are kept in the longitudinal direction at their respective predetermined positions by the pretension exerted by the system spring. However, as a result of the slightly smaller diameter thereof, the optical elements can move in the transverse direction in relation to the optics tube. In particular, the rod lenses can move with respect to one another and in relation to the optics tube in the transverse direction and can be tilted with respect to one another and in relation to the optics tube, as a result of which the optical axes of the rod lenses are no longer exactly flush with one another. Furthermore, the rod lenses can rotate about the longitudinal axis thereof, which can likewise lead to a deterioration in the imaging quality due to manufacturing-related tolerances, which the rod lenses are subject to.

The patent application DE 10 2013 101 650.2, which does not have a prior publication date, discloses the practice of fixing a rod lens received in the inside of an optics tube of an endoscope with the aid of a sleeve which can be welded to a desired position within the optics tube. The sleeve may comprise a ferromagnetic material. This enables a particularly simple handling when positioning the rod lens within the optics tube by virtue of the sleeve being pressed against the internal side of the optics tube by a magnet arranged outside of the optics tube and thereupon being welded to the optics tube in the position defined hereby.

SUMMARY OF THE INVENTION

It is an object of the present invention to specify an optics tube for an endoscope, a rod lens, a combination of an optics tube and at least one rod lens, and an endoscope, wherein fixed mounting of at least one rod lens in the optics tube can be achieved in a simple manner and wherein, in particular, decentering, tilting and/or rotating of the rod lens about the longitudinal axis thereof can be prevented.

This object is achieved by an optics tube for an endoscope, comprising, a magnet arrangement on one side of the optics tube which extends parallel to a longitudinal axis of the optics tube, by a rod lens comprising, a rod-shaped lens unit and a magnet arrangement on one side on a circumferential face of the lens unit, by a combination of an optics tube for an endoscope and at least one rod lens, wherein, on one side, the optics tube comprises a magnet arrangement which extends parallel to a longitudinal axis of the optics tube and wherein the rod lens comprises a rod-shaped lens unit and a magnet arrangement on one side on a circumferential face of the lens unit and by an endoscope comprising the combination of an optics tube and a rod lens.

Advantageous developments of the invention emerge from the dependent claims.

An optics tube according to the invention for an endoscope preferably has an elongate cylindrical shape and is embodied for receiving a rod lens arrangement, comprising at least one rod lens, of an endoscope in the interior of the optics tube. In particular, the optics tube is an optics tube of a rigid endoscope and is embodied for receiving the image carrier, constructed from a plurality of successively arranged rod lenses, of the endoscope. The optics tube is preferably metallic and consists of e.g. stainless steel.

According to the invention, the optics tube comprises a magnet arrangement which extends parallel to a longitudinal axis of the optics tube. The magnet arrangement of the optics tube is an arrangement of a ferromagnetic material or comprises at least one ferromagnetic material and can be embodied, for example, as a component connected to the optics tube, i.e. as a magnet, or as a magnet material applied to the optics tube, for example as a layer. In the transverse direction, the magnet arrangement is arranged on one side and therefore it is not arranged axially symmetrically with respect to the longitudinal axis of the optics tube. In particular, the magnet arrangement is embodied and arranged in such a way that, in respect of at least one longitudinal plane, which contains a longitudinal central axis of the optics tube, the ferromagnetic material is arranged completely or at least predominantly on one side of the longitudinal plane. The magnet arrangement can have soft or permanent magnetic properties. The magnet arrangement can have a continuous embodiment or consist of a plurality of segments or sections separated from one another by interruptions.

As a result of the fact that, on one side, the optics tube comprises a magnet arrangement extending parallel to the axis, it becomes possible to hold ferromagnetic elements, in particular at least one rod lens with a magnet arrangement assigned thereto, within the optics tube on that side which comprises the magnet arrangement or the predominant part of the ferromagnetic material of the magnet arrangement of the optics tube, and therefore it becomes possible to hold said ferromagnetic elements magnetically on the relevant side of the optics tube, substantially in a axis-parallel arrangement. Furthermore, this enables a particularly simple assembly of such elements within the optics tube, wherein a removal from the optics tube may continue to be possible in the case of repair.

The magnet arrangement of the optics tube is preferably embodied in the form of at least one strip extending parallel to the axis. In a particularly preferred manner, the at least one strip parallel to the axis substantially extends along the whole length of the optics tube, in particular along that region of the optics tube designed to receive rod lenses. In the axial direction, the at least one strip can be subdivided into a plurality of sections arranged parallel to the axis. To the extent that provision is made for a plurality of strips extending parallel to one another and parallel to the axis, said strips can be separated from one another by interruptions or gaps likewise extending parallel to the axis or said strips can rest very tightly against one another. What arranging the magnet arrangement or the ferromagnetic material in the form of one or more strips extending parallel to the longitudinal axis of the optics tube renders possible is that ferromagnetic elements, in particular rod lenses with corresponding magnet arrangements, arranged within the optics tube can be held with improved accuracy and safety in a linear arrangement within the optics tube, which linear arrangement extends parallel to the longitudinal axis of the optics tube.

In accordance with a preferred embodiment of the invention, the magnet arrangement is arranged on the external side of the optics tube. In order to enable a sufficient magnetic effect on magnetic elements arranged within the optics tube, the optics tube, in particular, is embodied with correspondingly thin walls or made of a non-ferromagnetic material. As a result of the magnetic arrangement being situated on the external surface of the optics tube, a restriction of the available installation space within the optics tube is avoided and an ideal use of the installation space available within an endoscope shank is made possible. Furthermore, this makes it easier to attach the magnet arrangement and hence the ferromagnetic material to the optics tube.

The magnet arrangement of the optics tube is preferably adhesively bonded to the optics tube. By way of example, the magnet arrangement can have a part-cylindrical form, the internal diameter of which is slightly larger than an external diameter of a cylindrically formed optics tube such that a gap for adhesion remains between the magnet arrangement and the optics tube, which gap is filled at least in part with adhesive for fixing the magnet arrangement on the optics tube. This makes it even easier to attach the magnet arrangement to the optics tube.

A rod lens according to the invention, which, in particular, is embodied as a rod lens of a relay lens system of an image carrier in a rigid endoscope, comprises a rod-shaped lens unit consisting of a single rod-shaped lens element or of a plurality of lens elements cemented to one another. The rod-shaped lens unit has a longitudinal axis, wherein a length of the lens unit in the direction of the longitudinal axis is greater than a diameter measured transversely with respect to the longitudinal axis. The optically effective faces of the rod lens are the two end faces of the lens unit and optionally interfaces between a plurality of lens elements situated in the interior of a lens unit composed of a plurality of lens elements. One or more lens elements can also be embodied as a flat rod. On the external side thereof, the rod-shaped lens unit has a circumferential face. The lens unit preferably has a rotationally symmetric, in particular at least sectionally cylindrical embodiment, wherein the longitudinal axis is the axis of symmetry of the lens unit. In the case of an at least sectionally cylindrically embodied lens unit, the circumferential face is the at least sectionally cylindrical lateral face of the lens unit.

A rod lens according to the invention comprises a magnet arrangement which is arranged on one side, i.e. transversely with respect to the longitudinal axis on one side of the circumferential face of the lens unit, and therefore not in an axially symmetric manner with respect to the longitudinal axis of the lens unit. The magnet arrangement of the rod lens is an arrangement of a ferromagnetic material or comprises at least one ferromagnetic material and can, for example, be embodied as a component connected to the lens unit of the rod lens, i.e. as a magnet, or as a magnet material applied to the circumferential face of the lens unit, for example as a layer. In particular, the magnet arrangement is embodied and arranged in such a way that, in respect of at least one longitudinal plane, which contains the axis of symmetry of a lens unit with a cylindrical embodiment, the ferromagnetic material is arranged completely or at least predominantly on one side of the longitudinal plane. In particular, the magnet arrangement only extends over a one-sided portion of the circumferential face of the lens unit. The magnet arrangement of the rod lens can have soft or permanent magnetic properties. The magnet arrangement can have a continuous embodiment or consist of a plurality of segments or sections separated from one another by interruptions. Within the scope of the present application, the unit or assembly made of the rod-shaped lens element or the lens elements cemented to one another and the magnet arrangement is referred to as a rod lens.

A rod lens according to the invention can be held magnetically in an optics tube embodied as described above, as a result of which, in an advantageous manner, a linear rod lens arrangement can be created, which, for example, is embodied as an image carrier of a rigid endoscope.

The magnet arrangement of the rod lens is preferably embodied as at least one strip arranged parallel to a longitudinal axis of the lens unit, which strip advantageously extends substantially along the whole length of the lens unit. The at least one strip can be interrupted in the longitudinal direction and have a plurality of sections. If a plurality of strips extending parallel to one another are provided, these strips can be separated from one another by interruptions or gaps likewise extending parallel to the axis or said strips can rest very tightly against one another. As a result of the magnet arrangement being embodied as at least one strip parallel to the axis, what can be achieved is a particularly secure hold of the rod lens or of the lens unit parallel to the axis in an optics tube embodied as described above, wherein, in particular, the longitudinal axes of a plurality of rod lenses or of the lens units of a plurality of rod lenses lie flush with one another.

The magnet arrangement of the rod lens is securely connected to the lens unit. In a particularly advantageous manner, the magnet arrangement is adhesively bonded to the circumferential face of the rod lens. To this end, the magnet arrangement can, for example, have a part-cylindrical form, wherein the internal diameter of the magnet arrangement is slightly larger than an external diameter of a cylindrically formed lens unit of the rod lens such that a gap for adhesion remains between the magnet arrangement and the lens unit, which gap is filled at least in part with adhesive for fixing the magnet arrangement. This makes it even easier to attach the magnet arrangement to the lens unit.

Furthermore, it is advantageous that the magnet arrangement is arranged on a region of the lens unit of the rod lens which is tapered in respect of the diameter. Since the radial outer region of a central section of the rod lens is not required for the image transmission in an image carrier of a rigid endoscope, such rod lenses are often embodied with a central region tapered in relation to the end regions. By arranging the magnet arrangement in this tapered region, an ideal use of the installation space available within the optics tube is made possible without substantially restricting the cross section of the lens unit of the rod lens required for the image transmission.

A combination, according to the invention, of an optics tube and at least one rod lens comprises an optics tube, in particular an optics tube of a rigid endoscope, wherein the optics tube is embodied as described above, and one or more rod lenses, which is or are embodied as described above. A combination of such an optics tube and at least one such rod lens enables the assembly of a rod lens arrangement, in particular of the image transmission system of a rigid endoscope, in a simple and safe manner and a secure hold of the at least one rod lens within the optics tube.

To the extent that a plurality of rod lenses are received in the optics tube, what the embodiment, according to the invention, of the optics tube and of the rod lenses can achieve in particular is that the longitudinal axes of the rod lenses or of the lens units of the rod lenses lie flush with one another and thereby form an optical axis of the rod lens arrangement, wherein decentering and tilting relative to the optical axis, as well as a rotation of the rod lenses about the longitudinal axis thereof can be prevented. Here, the longitudinal axes of the lens units of the rod lenses, and hence the optical axis, can deviate from the longitudinal central axis of the optics tube. In particular, a stable compensation of aberrations of the image carrier or of the whole optical system can be achieved, wherein the optical system moreover is particularly insensitive to tolerance-dependent deviations of the rod lenses, for example to deviations from a non-rotationally symmetric form. In particular, a particularly high resolution of the optical system can be ensured.

Preferably, the external radius of the at least one rod lens substantially equals the internal radius of the optics tube, at least in the region of the magnet arrangement of the rod lens. The external radius of the rod lens can, in particular, be that of the magnet arrangement of the rod lens, for example if the magnet arrangement has a partial cylindrical form. This enables a secure hold of the rod lens and an ideal use of the available installation space within the optics tube.

In accordance with a preferred embodiment of the invention, the magnet arrangement of the optics tube has permanent magnetic properties and the magnet arrangement of the rod lens has soft magnetic properties. In accordance with an alternative preferred embodiment of the invention, the magnet arrangement of the optics tube has soft magnetic properties and that of the rod lens has permanent magnetic properties. To this end, the magnet arrangement with permanent magnetic properties, of the optics tube or of the rod lens, comprises at least one permanent magnet. The magnet arrangements of the optics tube and of the rod lens can, in sections, have different designs. As a result of provision being made for at least one magnetic pairing of a permanent magnetic magnet arrangement on the optics tube with a soft magnetic magnet arrangement on the rod lens, or vice versa, a secure hold of the rod lens within the optics tube is made possible in a simple manner.

The permanent magnetic magnet arrangement of the optics tube or of the rod lens is preferably magnetized in the radial direction. To this end, a permanent magnet of the relevant magnet arrangement can, in particular, be arranged with radially directed magnetization. This enables a particularly secure hold of the rod lens within the optics tube.

In accordance with a further preferred embodiment of the invention, both the magnet arrangement of the optics tube and that of the rod lens have permanent magnetic properties and are magnetized for generating a magnetic attractive force between the optics tube and a rod lens arranged therein. This means that different poles of the permanent magnetic magnet arrangements of the optics tube and of the rod lens are directed toward one another. A particularly secure hold of the rod lens within the optics tube is also made possible by such a magnetic pairing.

In order to assemble one or more rod lenses according to the invention in an optics tube, according to the invention, of an endoscope, the respective magnet arrangements are initially applied, for example adhesively bonded, to the lens units of the rod lenses and to the optics tube. Here, within the meaning specified above, at least one magnetic pairing between the rod lenses and the optics tube is necessary. Thereupon the rod lenses, which as a preassembled assembly each comprise a rod-shaped lens unit and a magnet arrangement fastened thereon, are pushed, optionally with further optical elements such as spacers and stops, into the optics tube which was preassembled thus, with the arrangement and alignment being predetermined by the function of the optical system. As a result of the one-sided arrangement of the magnet arrangements, the rod lenses are attracted, flush with one another, to one side of the optics tube and held there by the magnetic force and due to the friction, increased by the magnetic force, between the rod lenses and the inner side of the optics tube. The rod lenses are also held in this arrangement when the endoscope is used and are thereby also fixed against a rotation about the longitudinal axis thereof. However, for repair purposes, the rod lenses can still be removed from the optics tube.

An endoscope according to the invention comprises an elongate optics tube, which is arranged within an elongate endoscope shank and can also reach into a head of the endoscope. The endoscope shank is embodied as a rigid endoscope shank, wherein a certain amount of bend may be admissible. By way of example, the optics tube can be embodied as an inner tube of endoscope optics, which are likewise referred to as endoscope here, or as system tube of an endoscope which may comprise e.g. work channels for endoscopic instruments or further channels. At least one rod lens, preferably a plurality of rod lenses, is arranged within the optics tube of the endoscope, wherein the optics tube and the at least one rod lens and the combination of the optics tube and the at least one rod lens are embodied as described above.

In the optics tube, the one or more rod lenses are held in contact with the wall of the optics tube on one side by magnetic forces. In the longitudinal direction, the rod lens or the rod lenses are fixed by frictional forces between the mutually touching surfaces of the at least one rod lens and the optics tube and, optionally, by pretension exerted by a system spring, arranged on a proximal side, on the arrangement of the rod lenses and possible further optical elements.

Tilting is prevented by the magnetic attractive forces exerted by the magnet arrangement, extending on one side parallel to the axis, of the optics tube and, to the extent that provision is made for a plurality of rod lenses, these are held in an arrangement flush with one another. Furthermore, the frictional forces and the magnet arrangements, applied to one side, of the optics tube and of the rod lenses also prevent a movement of the at least one rod lens in the circumferential direction of the optics tube and a rotation of the rod lens about the longitudinal axis thereof. As a result of the embodiment according to the invention of the optics tube and of the rod lenses received therein, it is possible to prevent, in particular, decentering, tilting and a rotation of the rod lenses about the longitudinal axis thereof, and a stable compensation of aberrations can be ensured, even during operation of the endoscope, as a result of which e.g. a particularly high resolution of the optical system can be made possible.

It is understood that the features mentioned above and yet to be explained below can be used not only in the respectively specified feature combination, but also in other combinations or on their own without departing from the scope of the present invention.

BRIEF DESCRIPTION OF THE DRAWINGS

Further aspects of the invention emerge from the following description of preferred exemplary embodiments and from the attached drawing. In detail:

FIGS. 2a and 2b show, in accordance with the first exemplary embodiment, schematic longitudinal sections of the optics tube with two rod lenses arranged therein, wherein FIG. 2b shows, in a magnified illustration, the section marked with a circle in FIG. 2a;

DETAILED DESCRIPTION OF THE INVENTION

Figure 1:
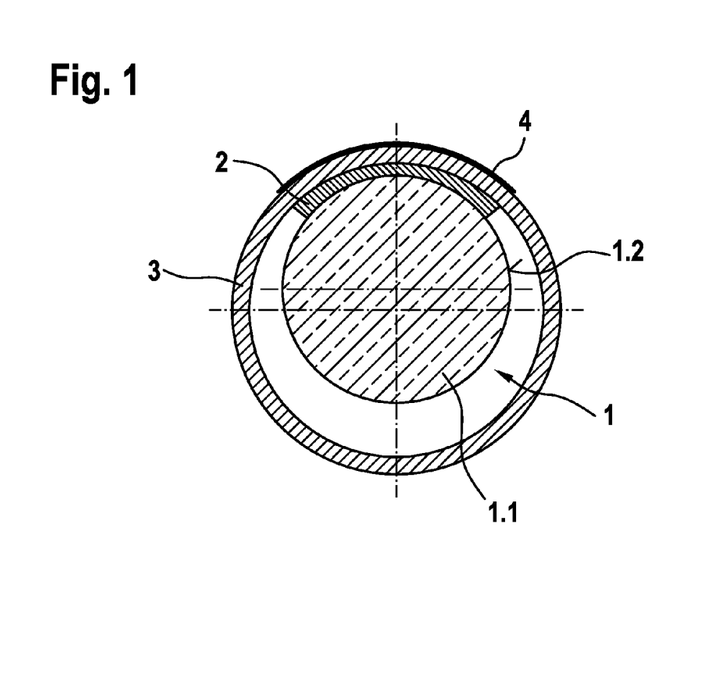
FIG. 1 shows a schematic cross section of an optics tube and a rod lens in accordance with a first exemplary embodiment of the invention.

As shown in FIG. 1, in accordance with a first exemplary embodiment of the invention, a magnet arrangement (magnet 2) has been adhesively bonded to the lateral face 1.2 of the cylindrical lens unit 1.1 of a rod lens 1. The optics tube 3 likewise comprises a magnet arrangement (magnet strip 4) adhesively bonded on one side. The magnet strip 4 takes up approximately a quarter of the circumference of the optics tube 3, i.e. approximately 90° as seen a longitudinal central axis of the optics tube 3. The magnet 2 rests against the internal side of the optics tube 3 in the region of the magnet strip 4 and likewise takes up approximately a quarter of the circumference of the lens unit 1.1, slightly more than a quarter or 90° in this case due to the slightly smaller external diameter of the lens unit 1.1 compared to the internal diameter of the optics tube 3. While the magnet strip 4 is embodied as a layer or as a flexible strip which rests against the external circumferential face of the optics tube 3 in the exemplary embodiment shown in FIG. 1, the magnet 2 has an internal radius which substantially corresponds to the external radius of the lens unit 1.1 of the rod lens 1 and has an external radius corresponding to the internal radius of the optics tube 3. Here, provision can be made for a gap for adhesion, filled with adhesive, between the magnet 2 and the lens unit 1.1; the magnet strip 4 is also fastened by adhesive bonding.

In order to securely hold the rod lens 1 in the optics tube 3, the magnet 2 and the magnet strip 4 are magnetically paired to one another in such a way that, either, the magnet 2 has permanent magnetic properties and the magnet strip 4 has soft magnetic properties or the magnet 2 has soft magnetic properties and the magnet strip 4 has permanent magnetic properties; or both the magnet 2 and the magnet strip 4 have permanent magnetic properties with unequal poles facing one another. This generates an attractive force between the magnet strip 4 and the magnet 2, wherein the optics tube 3 is made of a wall that is sufficiently thin or not to be ferromagnetic in order to enable a corresponding magnetic effect through the optics tube 3. It is possible to see from FIG. 1 that the lens unit 1.1 of the rod lens 1 is arranged asymmetrically within the optics tube 3, and so the axis of symmetry of the lens unit 1.1 is offset with respect to the longitudinal central axis of the optics tube 3.

Figure 2A:
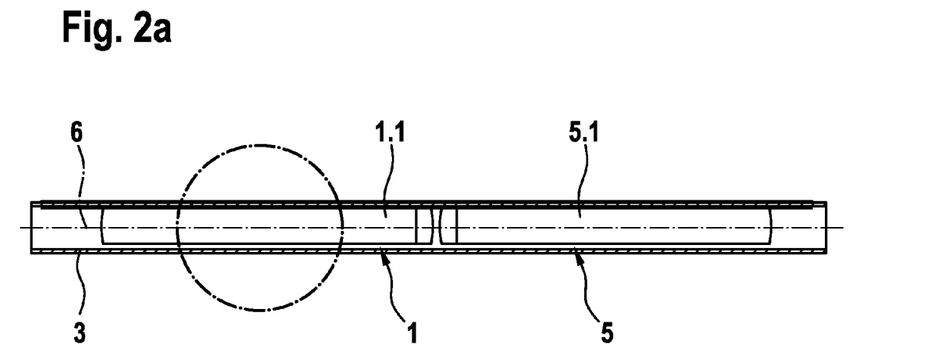
Figure 2B:
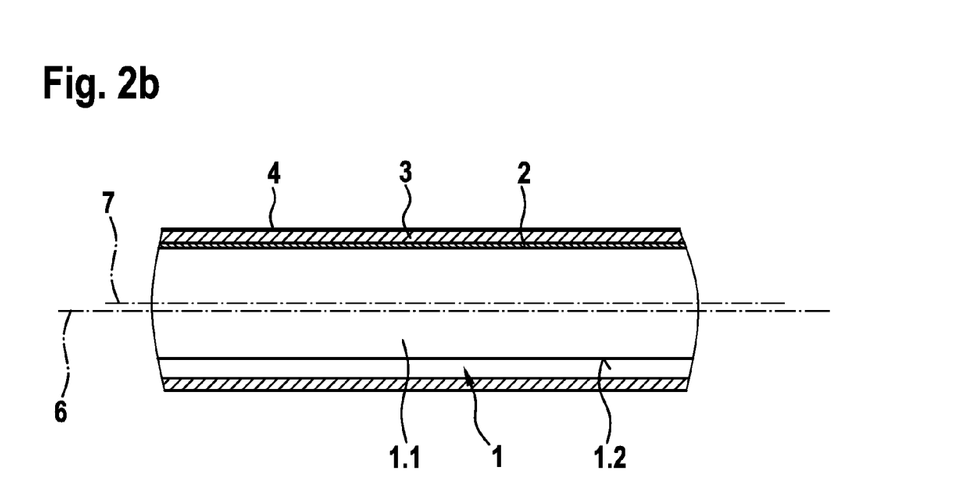

This is made clear in FIGS. 2a and 2b, in which the arrangement shown in a cross section in FIG. 1 is depicted in a longitudinal section. In accordance with FIG. 2a, two rod lenses 1, 5 are arranged within the optics tube 3, which rod lenses each comprise a cylindrical lens unit 1.1, 5.1 which in each case consists of an elongate rod part and a thin lens cemented thereto. The lens units 1.1, 5.1 face one another with the thin lenses and form an erecting system. The optics tube 3 can have more such erecting systems (not depicted here).

As indicated in FIG. 2a and depicted in a section in a magnified manner in FIG. 2b, the rod lens 1 is held on one side against the internal wall of the optics tube 3, wherein the longitudinal axis 7 of the rod lens 1, which is the axis of symmetry of the lens unit 1.1, is offset in relation to the longitudinal axis 6 of the optics tube 3, which is the longitudinal central axis of the optics tube 3. The magnet strip 4 arranged on one side on the external side of the optics tube 3 and the magnet 2 adhesively bonded on one side on the lens unit 1.1 of the rod lens 1 exert a magnetic attractive force on one another such that the rod lens 1 is securely held on the internal wall of the optics tube 3. Parallel to the axis, the magnet 2 extends substantially over the whole length of the lens unit 1.1. The rod lens 1 and the optics tube 3 have a cylindrical embodiment and the rod lens 1 is held parallel to the axis within the optics tube 3. The rod lens 5 is held within the optics tube in the same manner and, in the process, offset in the same direction as the rod lens 1 with the longitudinal axis thereof in relation to the longitudinal axis 6 of the optics tube. The axis of symmetry or longitudinal axis of the lens unit 5.1 is therefore flush with the axis of symmetry or longitudinal axis 7 of the lens unit 1.1 and forms the optical axis of the rod lens arrangement formed by the rod lenses 1, 5. This achieves a particularly tolerance-stable arrangement of the rod lenses 1, 5. In particular, a rotation of the rod lenses 1, 5 about the longitudinal axes thereof can be avoided, without a fixed connection being necessary between the rod lenses 1, 5 and the optics tube 3. Therefore, these can easily be pushed into the optics tube 3 and, if necessary, be removed again therefrom at a later time for repair purposes.

Figure 3:
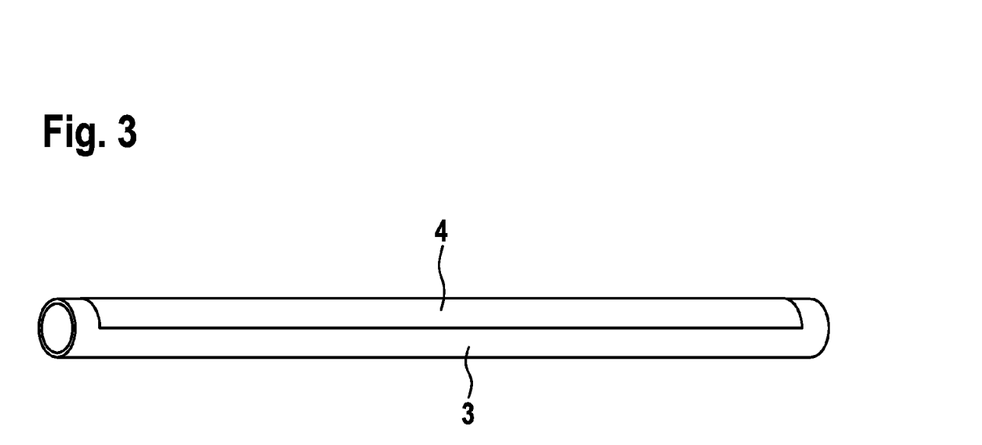
FIG. 3 shows a perspective view of the optics tube in accordance with the first exemplary embodiment.

FIG. 3 shows the optics tube 3 in accordance with the first exemplary embodiment of the invention in a perspective view. It can be seen from FIG. 3 that the magnet strip 4 extends substantially over the whole length of the optics tube 3 in the longitudinal direction of the optics tube 3.

Figure 4:
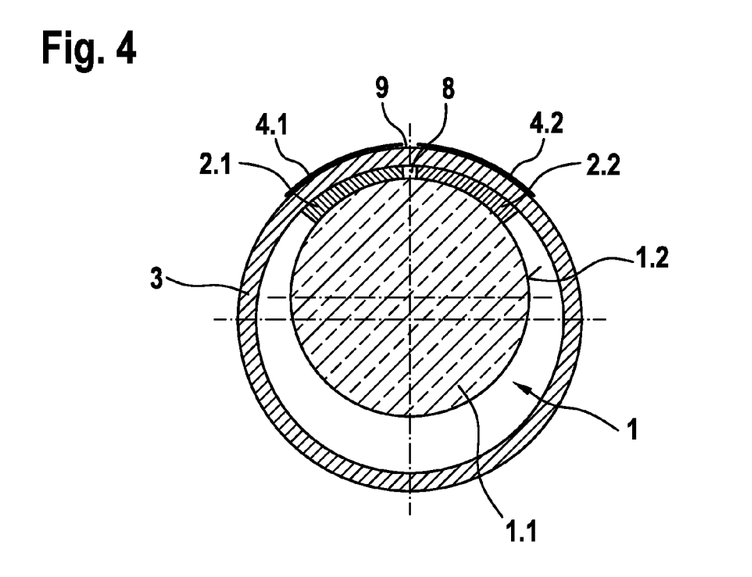
FIG. 4 shows a schematic cross section of an optics tube and a rod lens in accordance with a second exemplary embodiment of the invention.
Figure 5:
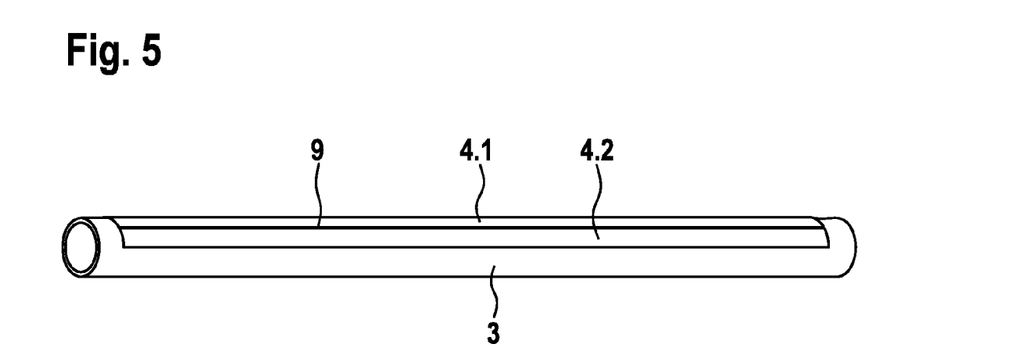
FIG. 5 shows a perspective view of the optics tube in accordance with the second exemplary embodiment.

In accordance with a second embodiment of the invention, which is depicted in FIGS. 4 and 5, the magnet arrangement of the rod lens 1 consists of two segments 2.1, 2.2, which are separated from one another by a gap 8 extending in the longitudinal direction of the rod lens 1. In a similar manner, the magnet arrangement of the optics tube 3 consists of two partial strips 4.1, 4.2, which both extend in the longitudinal direction of the optics tube 3 and are separated from one another by a gap 9. Otherwise, the exemplary embodiment depicted in FIGS. 4 and 5 is designed like the one depicted in FIGS. 1 to 3.

Figure 6:
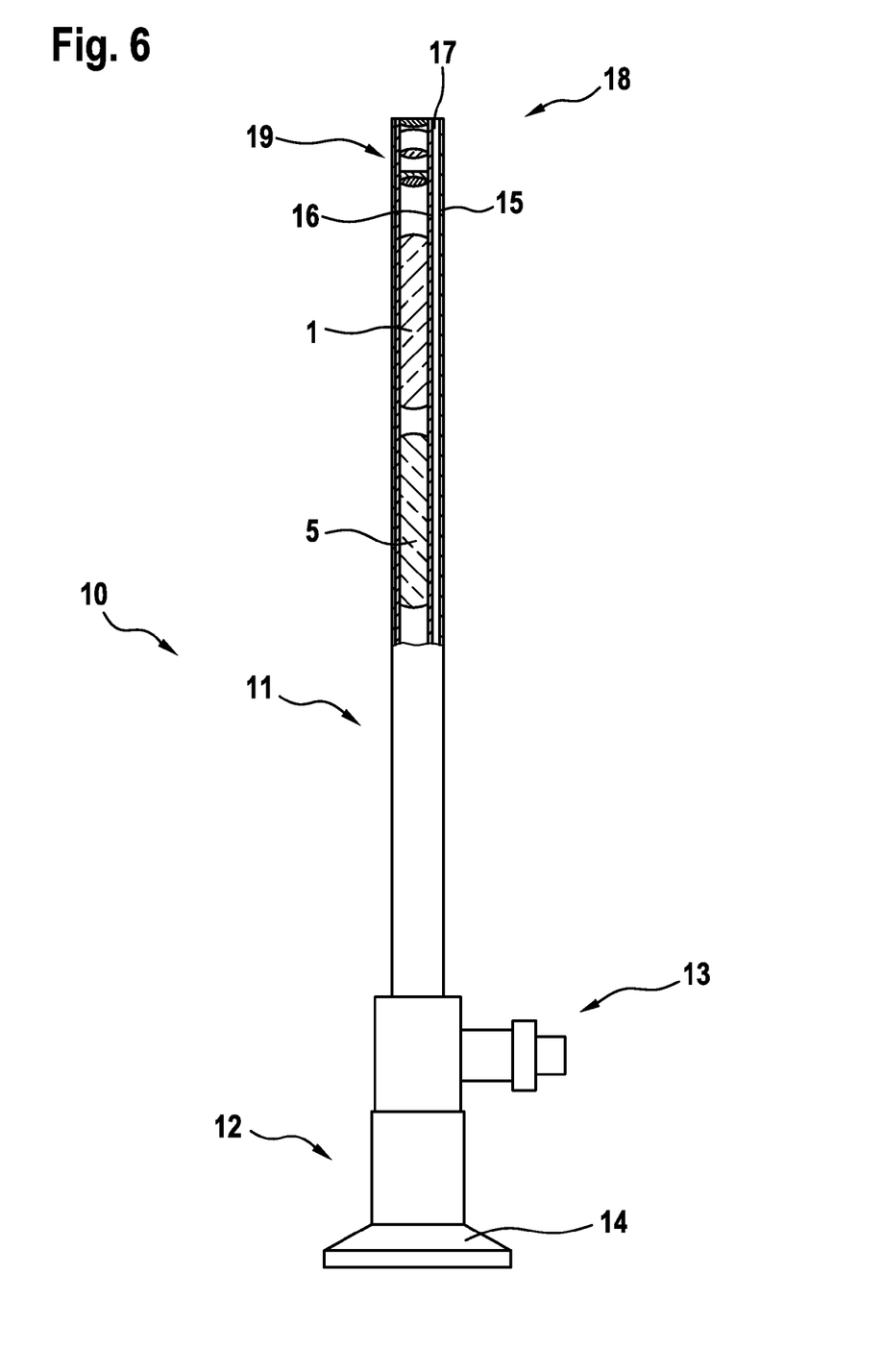
FIG. 6 shows a partly broken up side view of an endoscope.

FIG. 6 schematically depicts a rigid endoscope 10 with rod lenses in accordance with the above-described exemplary embodiments in an exemplary manner. The endoscope 10 comprises an elongate endoscope shank 11 embodied for insertion into a cavity in the interior of the body and an endoscope head 12 arranged at the proximal end of the endoscope shank 11, which endoscope head comprises a light connector 13 and an eyepiece with an eyecup 14. The optics tube 16 and optical waveguides 17 for transmitting the illumination light, coupled in the light connector 13, to the distal end region 18 of the endoscope 10 are arranged within the external tube 15 of the endoscope shank 11. An objective lens arrangement 19 and rod lenses 1, 5, which serve to transmit the endoscopic image cast by the objective lens arrangement 19 from the distal end region 18 to the proximal end region of the endoscope 10, are received in the interior of the optics tube 16. The optics tube 16 and the rod lenses 1, 5 are designed as described with respect to FIGS. 1 to 5 and merely depicted in a symbolic manner in FIG. 6.

Not all reference signs have been depicted in all figures for reasons of clarity. Reference signs not explained with respect to one figure have the same meaning as in the remaining figures.

LIST OF REFERENCE SIGNS

1 Rod lens
1.1 Lens unit
1.2 Lateral face
2 Magnet
2.1 Segment
2.2 Segment
3 Optics tube
4 Magnet strip
4.1 Partial strip
4.2 Partial strip
5 Rod lens
5.1 Lens unit
6 Longitudinal axis
7 Longitudinal axis
10 Endoscope
11 Endoscope shank
12 Endoscope head
13 Light connector
14 Eyecup
15 External tube
16 Optics tube
17 Optical waveguide
18 Distal end region
19 Objective lens arrangement

The invention claimed is:

1. An optical system for an endoscope, comprising: an optics tube having a magnet arrangement that extends parallel to a longitudinal axis of the optics tube; at least one rod lens having a rod-shaped lens unit and a magnet arrangement on a circumferential face of the lens unit; the magnet arrangement of the rod lens is formed as an elongate member aligned parallel to a longitudinal axis of the lens unit; and the magnet arrangement of the rod lens is magnetically paired with the magnet arrangement of the optics tube in order to hold the rod lens in place relative to the optics tube.

2. The optical system according to claim 1, wherein the magnet arrangement of the optics tube is embodied as at least one strip which is parallel to the longitudinal axis of the optics tube and extends substantially over the whole length of the optics tube.

3. The optical system according to claim 1, wherein the magnet arrangement of the optics tube is arranged on an external side of the optics tube.

4. The optical system according to claim 3, wherein the magnet arrangement of the optics tube is adhesively bonded to the external side of the optics tube.

5. The optical system according to claim 1, wherein the magnet arrangement of the rod lens is embodied as at least one strip which is directed parallel to a longitudinal axis of the lens unit.

6. The optical system according to claim 1, wherein the magnet arrangement of the rod lens is adhesively bonded to the circumferential face.

7. The optical system of claim 1, wherein an external curvature of the at least one rod lens equals an internal curvature of the magnet arrangement of the rod lens.

8. The optical system of claim 1, wherein the magnet arrangement of the optics tube has permanent magnetic properties and the magnet arrangement of the rod lens has soft magnetic properties.

9. The optical system of claim 8, wherein the magnet arrangement of the optics tube has radial magnetization.

10. The optical system of claim 8, wherein the magnet arrangement of the rod lens has radial magnetization.

11. The optical system of claim 1, wherein the magnet arrangement of the optics tube and the magnet arrangement of the rod lens have permanent magnetic properties and are magnetized for generating a magnetic attractive force between the optics tube and the rod lens.

12. The optical system of claim 1, wherein the rod-shaped lens unit is made of a rod-shaped lens element.

13. The optical system of claim 1, wherein the rod-shaped lens unit is made of a plurality of lens elements cemented to one another.

14. The optical system of claim 1, wherein the magnet arrangement of the optics tube has soft magnetic properties and the magnet arrangement of the rod lens has permanent magnetic properties.

15. The optical system of claim 14, wherein the magnet arrangement of the optics tube has radial magnetization.

16. The optical system of claim 14, wherein the magnet arrangement of the rod lens has radial magnetization.

* * * * *